US009474492B2

(12) United States Patent
Zhang et al.

(10) Patent No.: US 9,474,492 B2
(45) Date of Patent: Oct. 25, 2016

(54) ADAPTIVE ECG TRIGGER SIGNAL JITTER DETECTION AND COMPENSATION FOR IMAGING SYSTEMS

(71) Applicants: Hongxuan Zhang, Palatine, IL (US);
Dennis Steibel, Jr., Lake Zurich, IL (US)

(72) Inventors: Hongxuan Zhang, Palatine, IL (US);
Dennis Steibel, Jr., Lake Zurich, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 831 days.

(21) Appl. No.: 13/849,564

(22) Filed: Mar. 25, 2013

(65) Prior Publication Data

US 2013/0317336 A1     Nov. 28, 2013

Related U.S. Application Data

(60) Provisional application No. 61/649,992, filed on May 22, 2012.

(51) Int. Cl.
| A61B 5/00 | (2006.01) |
|---|---|
| A61B 5/0452 | (2006.01) |
| A61B 6/00 | (2006.01) |
| A61B 5/0456 | (2006.01) |

(52) U.S. Cl.
CPC ........... *A61B 5/7289* (2013.01); *A61B 5/0452* (2013.01); *A61B 5/7203* (2013.01); *A61B 5/7285* (2013.01); *A61B 5/0456* (2013.01); *A61B 5/7292* (2013.01); *A61B 5/7296* (2013.01); *A61B 6/541* (2013.01)

(58) Field of Classification Search
CPC ... A61B 5/7296; A61B 6/541; A61B 5/7292
See application file for complete search history.

(56) References Cited

U.S. PATENT DOCUMENTS

| 4,856,031 A | 8/1989 | Goldstein |
|---|---|---|
| 5,613,496 A | 3/1997 | Arand et al. |
| 6,226,231 B1 | 5/2001 | Kattan |
| 6,621,767 B1 | 9/2003 | Kattan |

(Continued)

FOREIGN PATENT DOCUMENTS

EP          2 339 755          6/2011

OTHER PUBLICATIONS

Paul D. Hale, et al., "Compensation of Random and Systematic Timing Errors in Sampling Oscilloscopes", IEEE Transactions on Instrumentation and Measurement, vol. 55, No. 6, Dec. 2006, pp. 2146-2154.

(Continued)

*Primary Examiner* — Serkan Akar (57) ABSTRACT

A system provides an image acquisition trigger signal compensated for signal processing time delay. An interface receives waveform signal data representing electrical activity of a patient heart over at least one heart beat cycle. A detector detects a particular point associated with a particular signal portion within successive heart beat cycles of the signal data. A first time variation detector provides a first timing adjustment signal in response to detected change in time of occurrence of the detected particular point. A second time variation detector provides a second timing adjustment signal in response to comparison of relative timing of the trigger signal and the detected particular point. An output processor generates the trigger signal in response to the detected particular point and the first timing adjustment signal and the second timing adjustment signal.

10 Claims, 11 Drawing Sheets

(56) References Cited

U.S. PATENT DOCUMENTS

| | | |
|---|---|---|
| 6,628,711 B1 | 9/2003 | Mathew et al. |
| 6,775,301 B1 | 8/2004 | Kroll et al. |
| 6,834,255 B2 | 12/2004 | Abrosimov et al. |
| 7,262,723 B2 | 8/2007 | Straussnig et al. |
| 7,418,210 B2 | 8/2008 | Moran et al. |
| 7,460,790 B2 | 12/2008 | Hauenschild et al. |
| 7,668,406 B2 | 2/2010 | Schnee et al. |
| 7,907,028 B1 | 3/2011 | Mack et al. |
| 7,912,117 B2 | 3/2011 | Tan et al. |
| 7,912,166 B2 | 3/2011 | Hsu et al. |
| 7,916,742 B1 | 3/2011 | Bugenhagen |
| 7,944,963 B2 | 5/2011 | Cases et al. |
| 7,945,009 B1 | 5/2011 | Liu et al. |
| 7,945,405 B2 | 5/2011 | Ishida et al. |
| 7,948,915 B2 | 5/2011 | Hinnant et al. |
| 7,953,579 B2 | 5/2011 | Hollis |
| 7,957,923 B2 | 6/2011 | Chao et al. |
| 7,961,778 B2 | 6/2011 | Buckwalter et al. |
| 7,983,375 B2 | 7/2011 | Dulger et al. |
| 7,991,046 B2 | 8/2011 | Sartschev et al. |
| 8,000,429 B2 | 8/2011 | Abe et al. |
| 8,005,181 B1 | 8/2011 | Steiner |
| 8,010,825 B2 | 8/2011 | Tamura |
| 8,014,680 B2 | 9/2011 | Lee et al. |
| 8,018,363 B2 | 9/2011 | Brooks et al. |
| 8,023,608 B2 | 9/2011 | Jang |
| 8,023,976 B2 | 9/2011 | Shao et al. |
| 8,032,350 B2 | 10/2011 | Hollis |
| 8,040,995 B2 | 10/2011 | Fukushima |
| 8,145,293 B2 | 3/2012 | Zhang et al. |
| 8,255,038 B2 | 8/2012 | Zhang |
| 2007/0255150 A1* | 11/2007 | Brodnick ............ A61B 5/0456 600/509 |
| 2007/0263672 A1 | 11/2007 | Ojala et al. |
| 2008/0211554 A1 | 9/2008 | Cho et al. |
| 2009/0072913 A1 | 3/2009 | Eikenbroek |
| 2010/0056897 A1* | 3/2010 | Zhang ................... A61B 6/541 600/407 |
| 2010/0074386 A1 | 3/2010 | Sakamoto et al. |
| 2010/0253793 A1 | 10/2010 | Auberger et al. |
| 2011/0182389 A1 | 7/2011 | Breems et al. |

OTHER PUBLICATIONS

Patrick G O Gmundson and Peter F. Driessen, "Zero-Crossing DPLL bit Synchronizer with pattern Jitter Compensation", IEEE Transactions on Communication, vol. 39, No. 4, 1991, pp. 603-612.

* cited by examiner

ADAPTIVE ECG TRIGGER SIGNAL JITTER DETECTION AND COMPENSATION FOR IMAGING SYSTEMS

This is a non-provisional application of provisional application Ser. No. 61/649,992 filed May 22, 2012, by H. Zhang et al.

FIELD OF THE INVENTION

This invention concerns a system for providing an image acquisition trigger signal compensated for signal processing time delay based on variation of timing of a heart electrical waveform relative to the trigger signal.

BACKGROUND OF THE INVENTION

ECG signals are utilized for triggering image scanning and data acquisition, such as of X-ray or ultrasound images and avoiding cardiac chamber tissue contraction distortion and other noise. However, known systems exhibit imprecision in image acquisition timing due to noise in trigger generation, clock jitter and analogue to digital conversion timing variation, causing inaccuracy in detection of a P wave, R wave and T wave in an ECG signal. Stable and accurate image scanning is desirable for analysis of cardiac function to detect cardiac diseases. Known imaging systems, such as X-ray and ultrasound imaging systems, for example, typically capture images randomly or with acquisition triggered in response to a time parameter. Known imaging systems use ECG signal synchronization to reduce patient artifacts and biological noise (heart beat and related patient movement). Image acquisition trigger signals in known systems are sensitive to jitter as well as phase and latency distortion from multiple sources. These sources include noise due to electrical surgery including energy discharge noise in ablation procedures and heart rate control device noise as well as pipeline transmission jitter due to a hardware transmission pathway. Further, the trigger error varies from system to system.

Known medical devices use different systems to trigger image data acquisition such as by using R wave detection, P wave detection or T wave detection. However such systems may have image acquisition trigger delay of 10-100 ms or jitter relative to cardiac activity or jitter due to analog to digital conversion, for example. Known signal detection and gating signal generation typically uses uniform sampling at a particular sampling rate, such as 2000 Hz, for sampling different portions of ECG signals, such as a P wave portion or QRS portion. Obtaining a high accuracy gating signal with low jitter based on uniform sampling may require a relatively high sampling rate for a signal, which results in over-sampling in portions of a signal and leads to increased timing jitter and uncertainty in a data transmission pipeline. A system according to invention principles addresses these deficiencies and related problems.

SUMMARY OF THE INVENTION

A system estimates and compensates for ECG trigger pulse timing jitter by using adaptive, controllable timing thresholds in ECG segment signal detection for synchronization as well as adaptive statistical calculation and correlation in closed-loop ECG image acquisition trigger signal generation. A system provides an image acquisition trigger signal compensated for signal processing time delay. An interface receives waveform signal data representing electrical activity of a patient heart over at least one heart beat cycle. A detector detects a particular point associated with a particular signal portion within successive heart beat cycles of the signal data. A first time variation detector provides a first timing adjustment signal in response to detected change in time of occurrence of the detected particular point. A second time variation detector provides a second timing adjustment signal in response to comparison of relative timing of the trigger signal and the detected particular point. An output processor generates the trigger signal in response to the detected particular point and the first timing adjustment signal and the second timing adjustment signal.

DETAILED DESCRIPTION OF THE INVENTION

A system estimates and compensates for image acquisition ECG trigger pulse timing jitter including P wave, R wave and T wave detection jitter and time stamp uncertainty, by adaptive statistical correlation. Closed-loop ECG triggering compensation is used in analogue signal and digital signal processing to provide accurate image acquisition gating pulse signals. The system employs adaptive, controllable timing thresholds in ECG segment signal detection and synchronization. Dynamic adaptive threshold based ECG segment waveform analysis and estimation is used to improve image quality particularly in a fast scanning system performing non-rigid tissue image acquisition. The ECG trigger signal jitter compensation provides non-uniform image acquisition trigger signals (for cardiac activity scanning) in response to programmable cardiac function selection and sequential triggering signal generation.

The system automatically adaptively and dynamically compensates for signal generation and transmission jitter and latency to improve accuracy of time stamps associated with acquired images. The system detects portions of an ECG waveform for image acquisition gating and synchronization signal generation reducing effect of digitization time jitter, data transmission pipeline time jitter and processing jitter by generating jitter and latency compensated image acquisition trigger signals.

Figure 1:
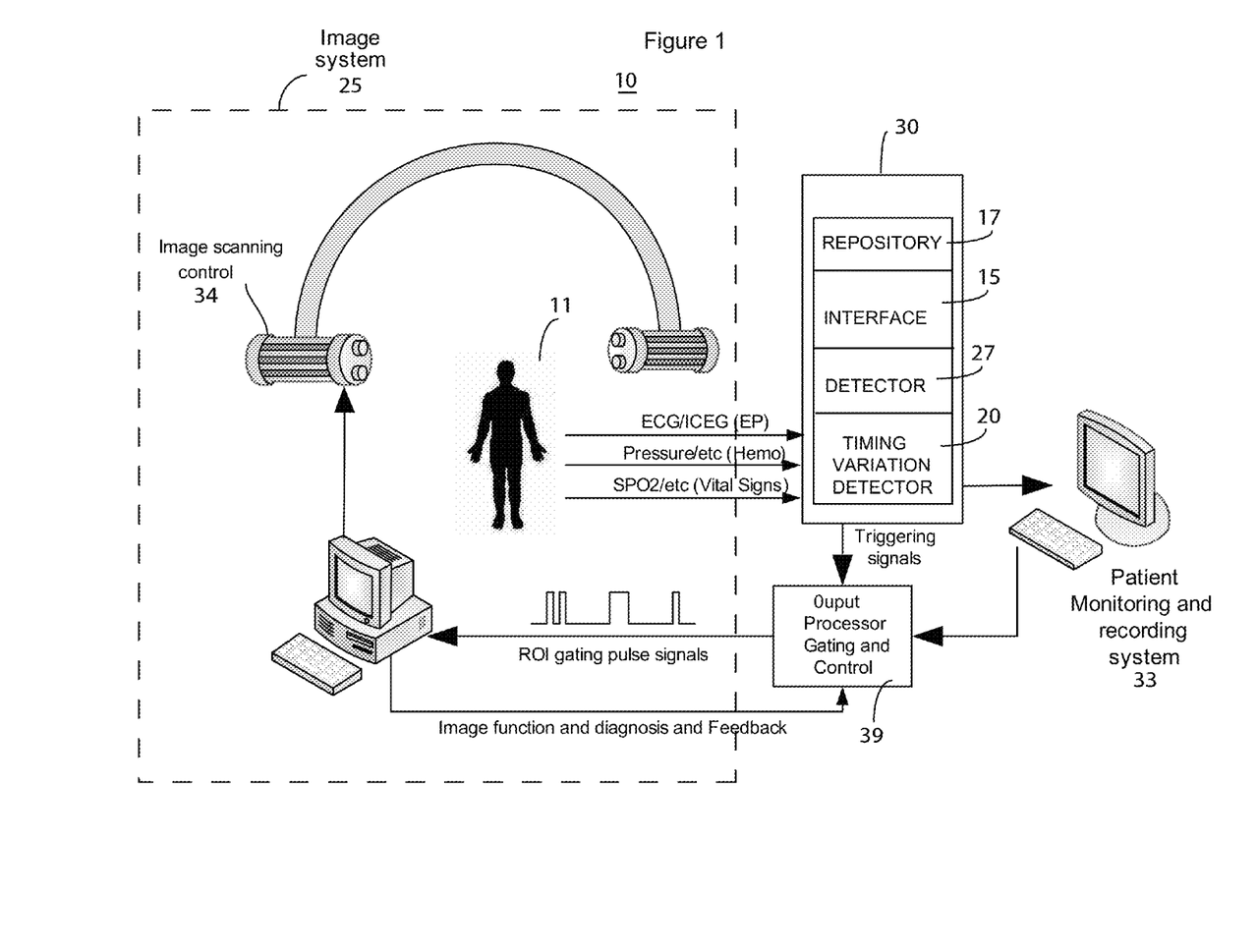
FIG. 1 shows a system for providing an image acquisition trigger signal compensated for signal processing time delay, according to invention principles.

FIG. 1 shows system 10 for providing an image acquisition trigger signal compensated for signal processing time delay. System 10 employs at least one computer, microprocessor, programmed logic device or other processing devices comprising output processor 39 and device 30 including repository 17, interface 15, detector 27 and timing variation detectors 20. Surface ECG and Intra-cardiac electrogram (ICEG) signals having an amplitude representing electrical activity of a heart over time, and other vital sign signals including blood pressure, SPO2 blood oxygen saturation, temperature and heart rate signals are acquired from patient 11 by processing device 30 and conditioned by device 30 (for voltage level, lead construction variation and calibration by buffering, digitization and conditioning) based on patient context and a clinical application being performed. The processed signals from unit 30 are provided to patient monitoring system 33.

Interface 15 receives waveform signal data representing electrical activity of a patient heart over at least one heart beat cycle. Detector 27 detects a particular point associated with a particular signal portion within successive heart beat cycles of the signal data. Timing variation detectors 20 includes a first time variation detector, a second time variation detector and a third time variation detector. A first time variation detector provides a first timing adjustment signal in response to detected change in time of occurrence of the detected particular point. A second time variation detector provides a second timing adjustment signal in response to comparison of relative timing of the trigger signal and the detected particular point. A third time variation detector provides a third timing adjustment signal in response to comparison of relative timing of the trigger signal and a timing signal associated with time of acquisition of an image received from image acquisition system 25. Output processor 39 generates the trigger signal in response to the detected particular point and the first timing adjustment signal, the second timing adjustment signal and the third timing adjustment signal.

System and imaging control unit 34 controls operation of one or more imaging devices 25 for performing image acquisition of patient anatomy in response to user command. Imaging devices 25 may comprise a mono-plane or biplane X-ray imaging system. The units of system 10 intercommunicate via a network. At least one repository 17 stores X-ray medical images and studies for patients in DICOM compatible (or other) data format and vital sign signal data. A medical image study individually includes multiple image series of a patient anatomical portion which in turn individually include multiple images.

Processing device 30 buffers, filters and digitizes ECG and ICEG data from patient 11. Device 30 detects P wave, Q wave, R wave, T wave, S wave and U wave segments of processed ECG and ICEG data by detecting peaks within the received data using a known peak detector and by segmenting the processed ECG and ICEG data into windows where the waves are expected and by identifying the peaks within the windows. The start point of a wave, for example, is identified by a variety of known different methods. In one method a wave start point comprises where the signal crosses a baseline of the signal (in a predetermined wave window, for example). Alternatively, a wave start point may comprise a peak or valley of the signal. The baseline of the signal may comprise a zero voltage line if a static (DC) voltage signal component is filtered out from the signal. Device 30 includes a timing detector for determining time duration between the signal peaks and valleys. The time detector uses a clock counter for counting a clock between the peak and valley points and the counting is initiated and terminated in response to the detected peak and valley characteristics.

Triggers signals (including peak time of P wave, Q wave, R wave, S wave, T wave) are utilized by units 30, 33 and 39 to control and manipulate image acquisition by system 25. The accuracy of trigger pulse generation is affected by factors including, a) signal portion (such as peak or valley) detection and jitter; b) the trigger signal delay and jitter relative to corresponding heart activity due to circuitry and c) gating signal transmission and data pipeline distortion and jitter. The following function summarizes these error sources:

Gating_signal_jitter=Gating_detection−creation_jitter⊕Circuitry_uncertainty_jitter⊕data_pipeline_jitter In which, Gating_detection−creation_jitter is the jitter and distortion from signal portion detection; Circuitry_uncertainty_jitter is analogue and digital circuitry electronic delay and uncertainty, which includes timing jitter from Analog to Digital Conversion (ADC), filtering, and other hardware sources; data_pipeline_jitter represents data jitter and timing uncertainty from data transmission, such as Ethernet, RS232, Serial transmission.

Assuming the timing jitter distribution is a normal distribution and the jitter of the three main sources is: $\pm\alpha$, $\pm\beta$, and $\pm\gamma$, the gating signal jitter of a signal provided to an image acquisition system is, $$\text{Gating\_signal\_jitter} = (T_1 \pm \alpha) + (T_2 \pm \beta) + (T_3 \pm \gamma)$$
$$= T_1 + T_2 + T_3) \pm \alpha \pm \beta \pm \gamma$$
$$= T_{delay} \pm (\alpha + \beta + \gamma)$$

In which T1, T2, T3 represent timing of a desired point within a waveform for image acquisition $T_{delay}$ is average time delay between a patient trigger signal provided to an image acquisition system. Overall, the maximum timing jitter and uncertainty are $\alpha+\beta+\gamma$, for which different kinds of compensation are provided. The sources $\pm\alpha$, $\pm\beta$, and $\pm\gamma$ may be time varying and differ from case to case. Hence, an adaptive dynamic compensation system is provided.

System 10 integrates both a patient real time signal monitoring and recording system 33 and image acquisition system 25. Imaging system 25 synchronizes image acquisition using a signal point or signal portion (such as R wave, T wave and P wave) to generate gating signals. Output processor 39 adaptively generates uniform and non-uniform gating trigger signals compensating for circuit time delay and jitter and uses patient monitoring system 33 and device 30 signals in response to a clinical application type. Output processor 39 uses a feedback signal from imaging system 25 indicating circuit time delay and jitter in gating signal control and generation.

Figure 2:
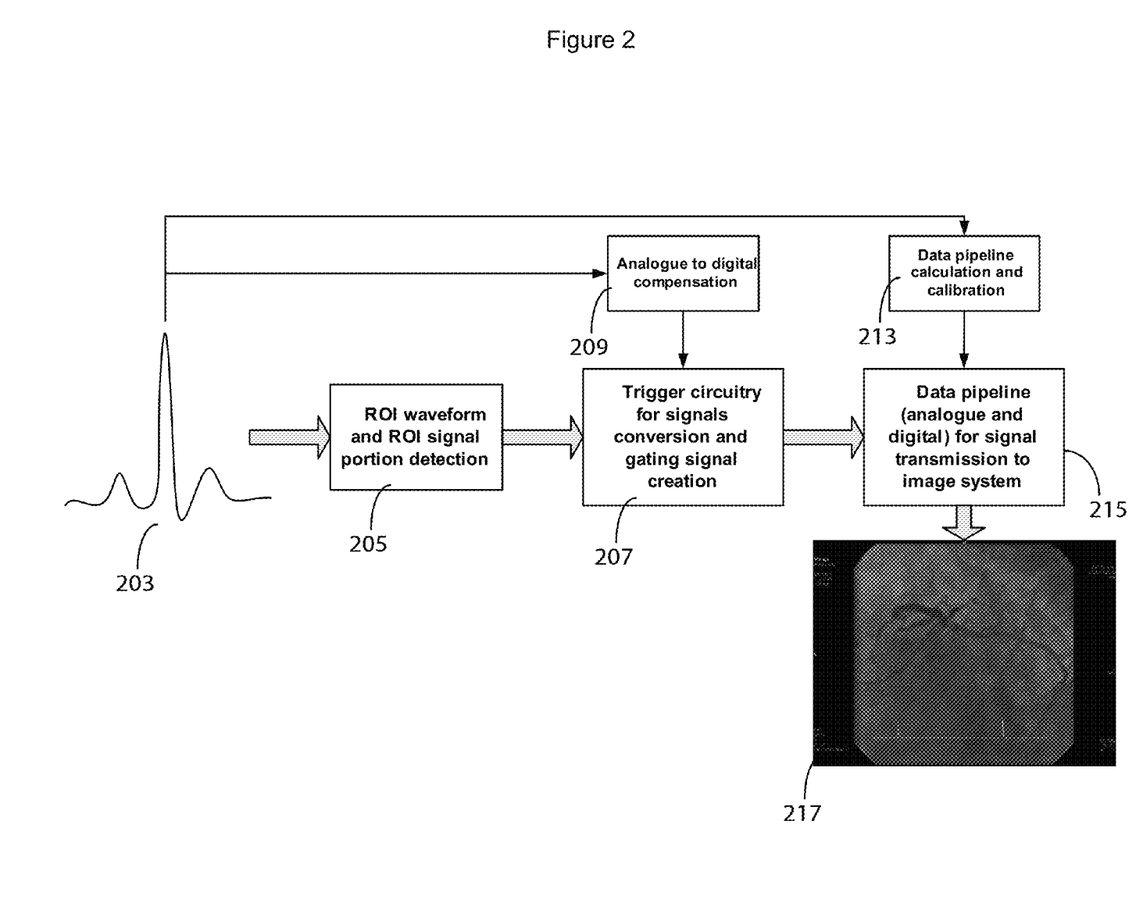
FIG. 2 shows different jitter sources occurring in patient signal acquisition and filtering and trigger signal generation, according to invention principles.

FIG. 2 shows different jitter sources occurring in patient signal acquisition and filtering and adaptive compensated trigger signal generation. System units 207 and 213 employ different compensation methods. Specifically, unit 207 determines and applies trigger delay or advance to compensate for both ECG signal 203 signal portion waveform (including peak or valley) detection jitter 205 as well as to offset ECG signal 203 analogue to digital conversion circuit jitter 209. Unit 215 determines and applies trigger delay or advance to a compensated trigger signal from unit 207 to compensate for ECG signal 203 data pipeline signal transmission delay 213 and reduces the jitter in data transmission and coding. Unit 215 provides a resultant trigger signal output for acquisition of image 217 by imaging system 25. Other types of jitter may also be compensated in a similar fashion. Unit 217 provides a trigger signal to image acquisition system 25. The trigger signal is compensated for jitter sources 205, 209 and 213. The jitter sources introduce jitter due to signal acquisition, filtering and trigger signal generation delay including waveform portion detection and data transmission distortion.

Figure 3:
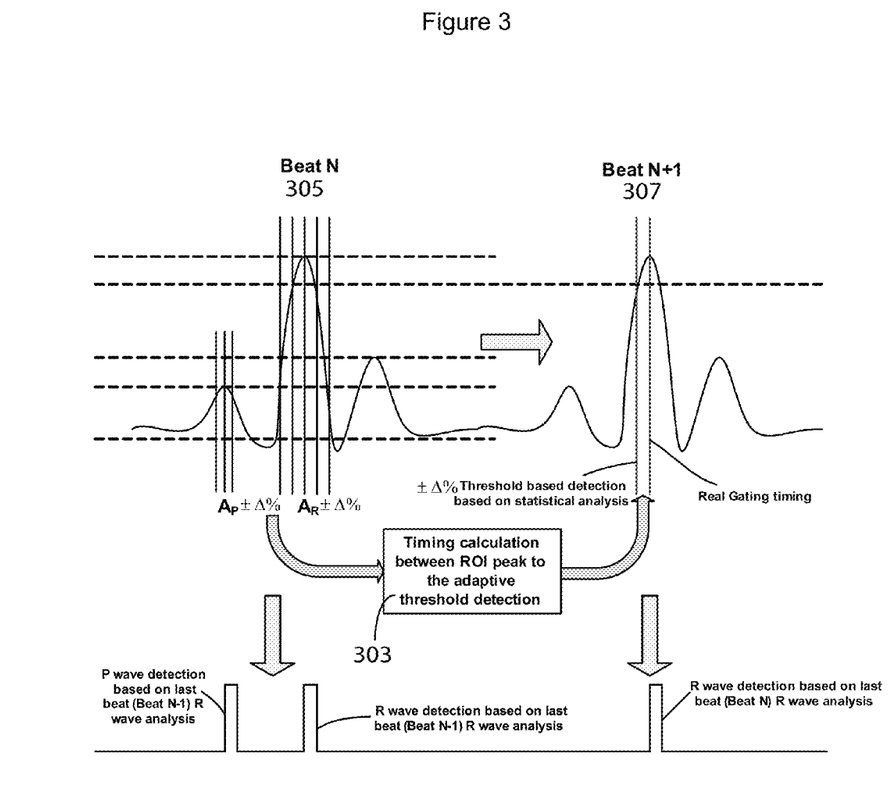
FIG. 3 shows an adaptive threshold based ECG waveform portion detection system, according to invention principles.

FIG. 3 shows an adaptive threshold based ECG waveform portion detection system. Processing device 30 advantageously calculates an adaptive weighted combination time threshold for accurate ECG signal portion detection. Device 30 (FIG. 1) performs programmable ECG signal portion detection employing timing unit 303 for time variation detection and providing a timing adjustment signal in response to detected change in time of occurrence of a detected particular point. Device 30 is programmable, adjustable and controlled in a real time mode, for both P wave detection and R wave detection in Beat N 305 while limited to just R wave detection in Beat N+1 307, for example. Device 30 calculates waveform portion detection times and statistically analyzes a previous heart beat to determine a waveform portion time stamp for acquisition of the portion in a current heart beat. In a different embodiment, beat N 305 is not necessarily the nearest neighbor heart beat of a current heart beat N+1 307 as long as it is the same rhythm episode.

Device 30 employs a method to determine a heart signal waveform portion or point timed from a previous portion in real time. Device 30 acquires signal data comprising a previous heart cycle or multiple previous heart cycles (the number of cycles depends on noise level as the better the signal quality, the less heart beats are needed). Device 30 determines parameters from heart cycle signal data, including waveform portion or point peak maximum amplitude, and amplitude of 90% maximum, 80% maximum, . . . , 20%, 10% maximum on both sides near a region of interest (ROI) portion of the heart cycle signal data waveforms.

Figure 4:
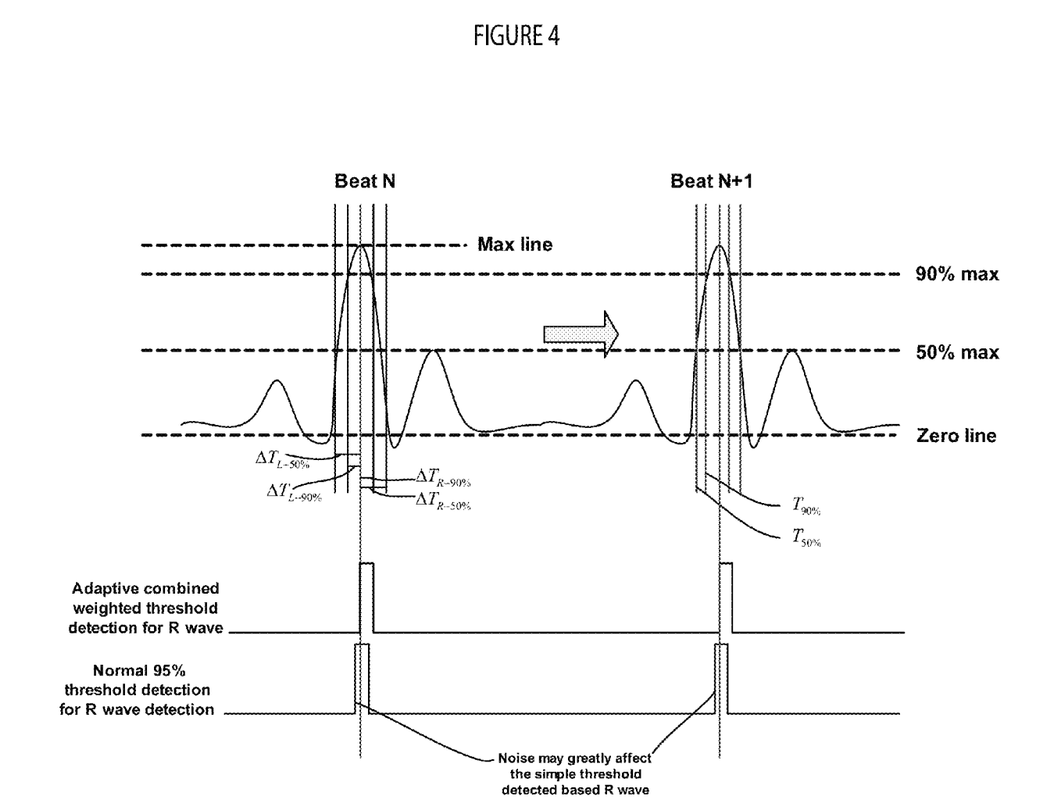
FIG. 4 shows R wave detection and trigger pulse generation, according to invention principles.

FIG. 4 shows signal R wave detection and trigger pulse generation indicating time interval points corresponding to left and right amplitude levels 10% and 50% below peak comprising $\Delta T_{L-50\%}$, $\Delta T_{L-90\%}$, $\Delta T_{R-90\%}$, $\Delta T_{R-50\%}$. Time interval points for an R wave (100% amplitude at peak point) are $\Delta T_{L-10\%}$, $\Delta T_{L-20\%}$, . . . , $\Delta T_{L-80\%}$, $\Delta T_{L-90\%}$, $\Delta T_{R-90\%}$, $\Delta T_{R-80\%}$, . . . , $\Delta T_{R-20\%}$, $\Delta T_{R-10\%}$, for example. Device 30 detects amplitude changes in a current heart signal, 10% of maximum (of previous heart cycles), 20% of maximum, . . . , 90% of maximum with corresponding timings are $T_{10\%}$, $T_{20\%}$, . . . , $T_{90\%}$. Device 30 calculates a time stamp of a current waveform portion start point. The accuracy of the time stamp calculation of a waveform point is indicated by closeness of a statistical confidence of a threshold calculation, such as $\Delta T_{L-90\%}$ and $\Delta T_{R-90\%}$. This facilitates achieving less than 100 uS error in image acquisition trigger timing.

The system in one embodiment employs the function, $$T_{ROI}=T_{10\%}+(\alpha_1 \cdot \Delta T_{L-10\%}+\beta_1 \cdot \Delta T_{R-10\%})$$

Where $T_{ROI}$ is a time stamp for a current heart cycle (cycle N+1), Rwave peak is determined based on time stamp of a time point $T_{10\%}$ representing a 10% amplitude level of the R wave of cycle N+1 plus an adjustment derived using the prior heart cycle N. L and R represent left side and right side (relative to R peak) time duration. Device 30 uses previous heart cycles and cycles (such N−1, N) and cycle N+1 so R wave peak position may be estimated one cycle earlier, which facilitates compensation of jitter.

Figure 5:
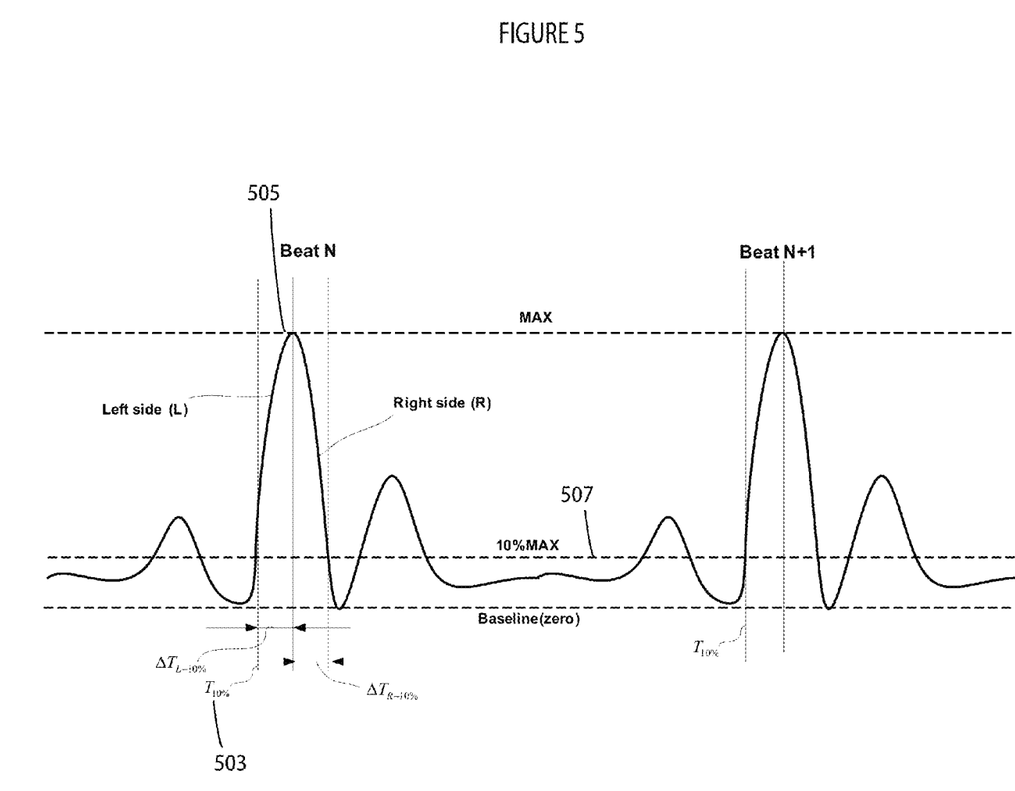
FIG. 5 shows waveform peak position estimation, according to invention principles.

FIG. 5 shows waveform peak position estimation. For example, $T_{10\%}$ (503)=120 second (a recording time (time stamp), from a beginning of data acquisition).

$\alpha_1 \cdot \Delta T_{L-10\%}+\beta_1 \cdot \Delta T_{R-10\%}$ is an estimate of R wave 505 duration from 10% MAX level 507 to the R wave 505 peak of previous cycle (N), α and β here are 0.6 and 0.4 since a Left rising edge is faster than the right rising edge. In cycle N, R wave duration, $\Delta T_{L-10\%}$ is 120 Ms and $\Delta T_{R-10\%}$ is 70 ms so the calculation $\alpha_1 \cdot \Delta T_{L-10\%}+\beta_1 \cdot \Delta T_{R-10\%}$ is 0.6×120+ 0.4×70=100 ms and time ROI from 10% MAX to R wave peak is 100 ms plus the time reference from time of start of recording data (which is 120 second), a new R wave peak time is predicted as 120.1 seconds.

System 10 uses amplitudes at the, 10%. 20% . . . 90% levels to categorize a whole R wave into 10 levels by amplitude and determines the time of occurrence of each corresponding level (T). In addition, system 10 employs cycle N−1 to estimate time of occurrence of an R wave peak, for example, of cycle N+1, 2 cycles later using, $$T_{ROI}=2T_{RR}+T_{10\%}+(\alpha_1 \cdot \Delta T_{L-10\%}+\beta_1 \cdot \Delta T_{R-10\%})$$

where $T_{10\%}$ is the time of 10% MAX amplitude level in the cycle N−1, $\alpha_1 \cdot \Delta T_{L-10\%}+\beta_1 \cdot \Delta T_{R-10\%}$ is the R wave relative time position to $T_{10\%}$ in cycle N−1; $2T_{RR}$ is a two cycle time length.

If a requirement is 1-2 ms max jitter, a 10% threshold is enough for calculating a time stamp of a waveform portion or point of a current heart signal (a time stamp of a waveform portion or point is also used to determine image acquisition trigger pulse timing), $$T_{ROI}=T_{10\%}+(\alpha_1 \cdot \Delta T_{L-10\%}+\beta_1 \cdot \Delta T_{R-10\%})$$

where $\alpha_1+\beta_1=1$, α and β are weight coefficients for determination of a time stamp of a waveform point. In a clinical application example, α=0.55 and β=0.45, because a depolarization procedure is faster than repolarization, however a user is able to adjust weight coefficients based on type of clinical application.

If a requirement is 200-500 uS maximum jitter, a 10% threshold is sufficient for calculating a time stamp of a waveform portion or point and $$T_{ROI}=T_{50\%}+(\alpha_5 \cdot \Delta T_{L-50\%}+\beta_5 \cdot \Delta T_{R-50\%})$$

where $\alpha_5+\beta_5=1$. A numerical sequence of weight coefficients is user definable and optimal timing of jitter may require a high data sample rate, such as 5-10K Hz. If a signal portion has distortion, or a signal portion is detected in the presence of noise, more amplitude thresholds may be employed and combined to determine a waveform portion time stamp or point time stamp from data from previous heart cycles, $$T_{ROI} = \sum_{i \in threshold\_range} T_{i*10\%} + (\alpha_i \cdot \Delta T_{L-i*10\%} + \beta_i \cdot \Delta T_{R-i*10\%})$$

where threshold_Range represents how many thresholds are employed in a calculation and corresponding weight coefficients are used for selected thresholds.

Returning to FIG. 4, which shows a 50% and 90% combined $T_{ROI}$ calculation in an R wave. However, other portions e.g. P wave, T wave portions may be used, for example. An image acquisition trigger pulse derived using a 95% threshold for R wave peak detection may achieve jitter less than 100 uS, for example. An adaptive combined weighted threshold calculation may use a 95% threshold, but noise in the clinical environment, such as patient movement, electrical noise, decreases trigger pulse timing accuracy. In a noisy environment, system 10 generates a timing pulse by averaging over multiple heart cycles. System 10 employs a single cycle statistical timing analysis together with heart rate variability analysis to predict and compensate for trigger pulse timing errors. A heart rhythm variation is also taken into account during cardiac peak prediction. For example, a prolonged trend in QRS rate is used in ECG R wave detection for image acquisition.

Figure 6:
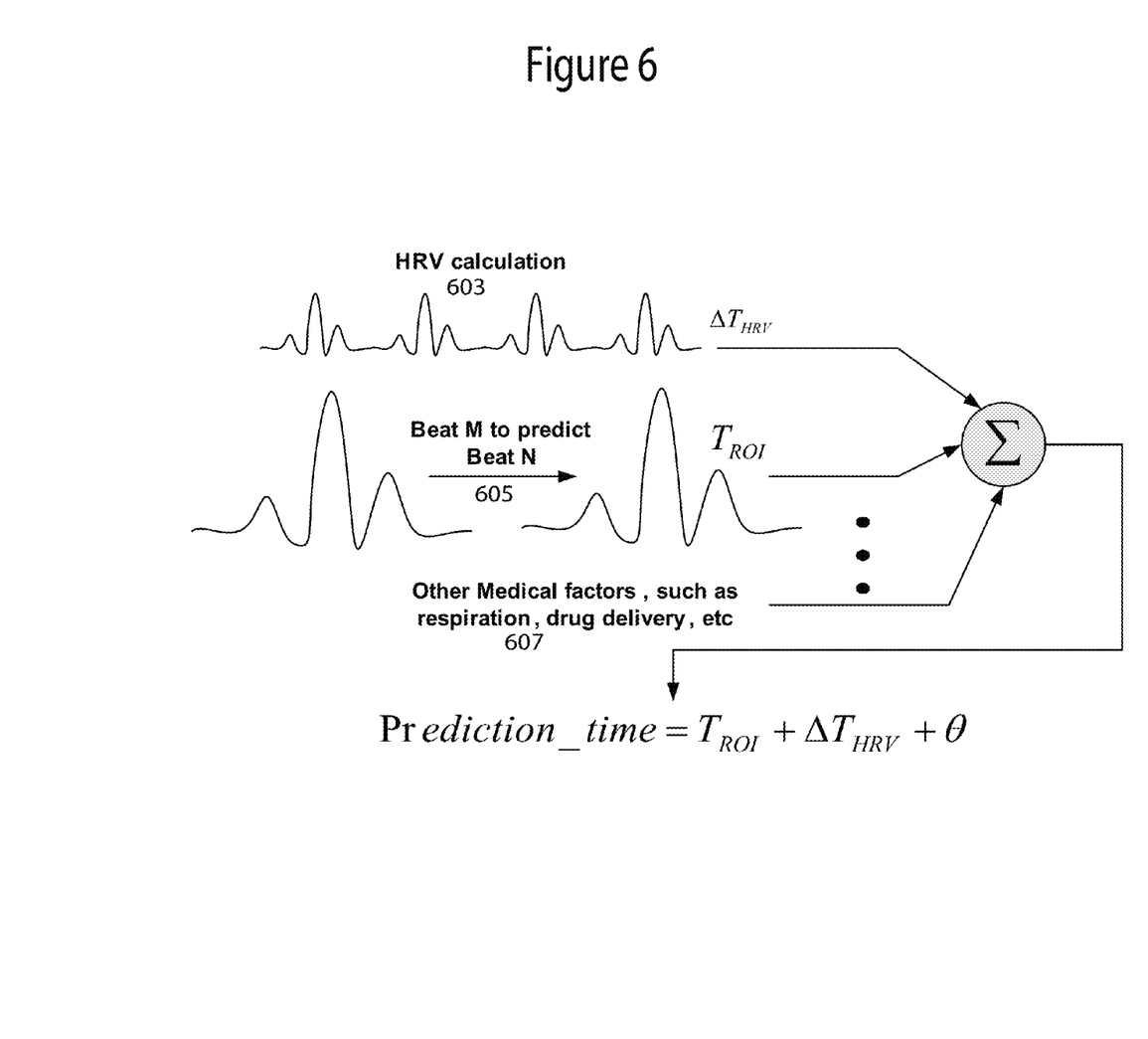
FIG. 6 shows a heart rate variability method integrated with a statistical prediction method for waveform peak detection and prediction, according to invention principles.

FIG. 6 shows heart rate variability method 603 integrated with a statistical prediction method 605 for Beat N waveform peak detection and prediction. Together with these methods, other medical factors 607 may be used according to patient medical conditions, such as drug delivery, electrical treatment. $T_{ROI}$ is a prediction time derived by statistical calculation from Beat M (early beat) and $\Delta T_{HRV}$ is Heart beat variation (e.g. if positive, it means an R wave recurrence interval is prolonged), θ is another factor based time compensation. A prediction time is calculated at 50-100 uS, using the following function, $$\text{Prediction\_time} = T_{ROI} + \Delta T_{HRV} + \theta$$

Figure 7:
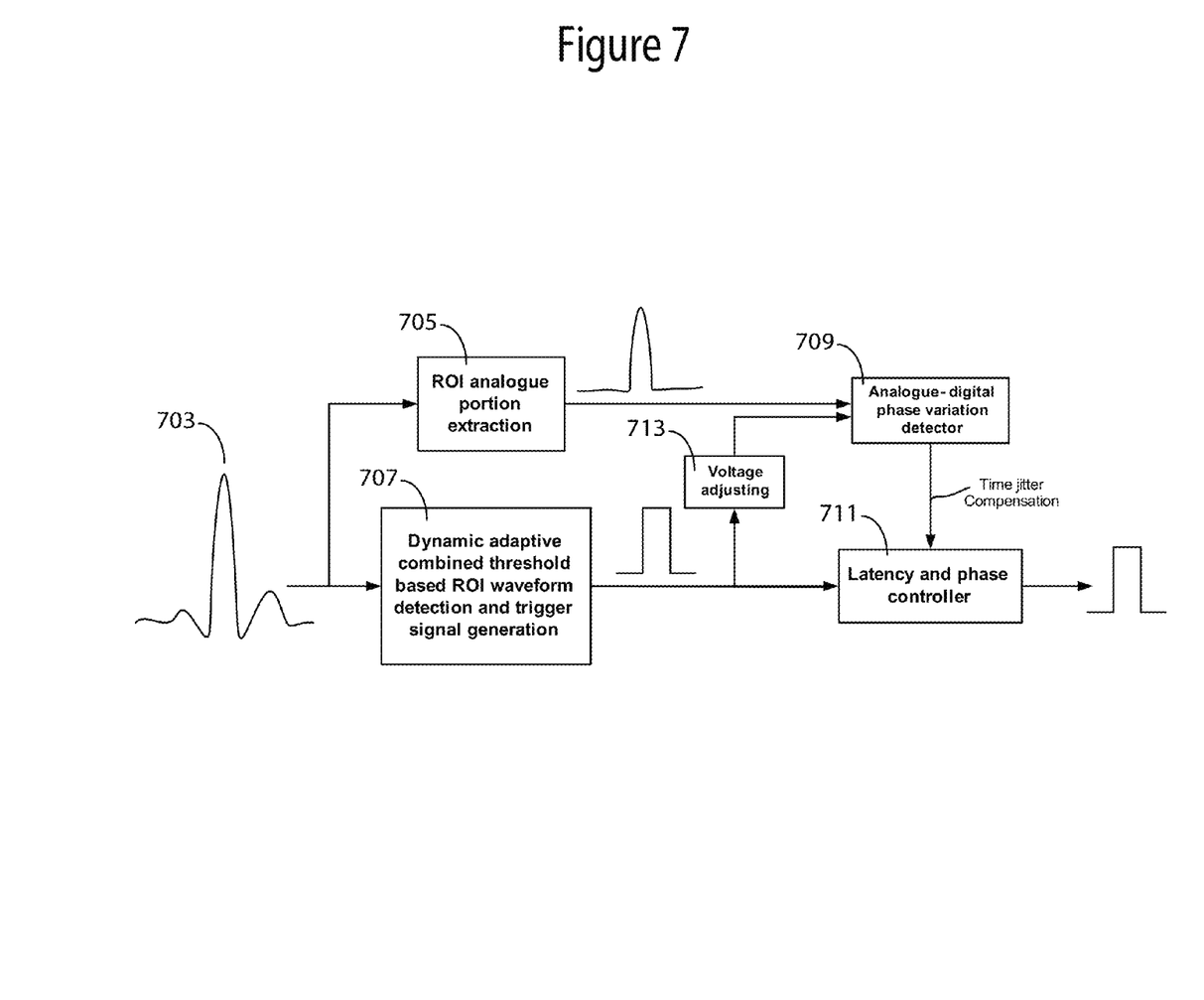
FIG. 7 shows circuit timing compensation in response to time clock variation, signal component characteristic variation, sampling rate changes, signal noise and circuit layout induced variation, according to invention principles.

FIG. 7 shows circuit timing compensation in response to time clock variation, signal component characteristic variation, sampling rate changes and signal noise and circuit layout induced variation. Hardware circuitry provides a further source of ECG trigger signal jitter. Trigger pulse latency compensation is provided by comparison of an original ECG signal with a trigger pulse. ECG signal 703 is coupled to a dynamic adaptive ROI detection module 707 and to a signal portion extraction unit 705. ROI detection module 707 generates a TTL or CMOS level trigger pulse, for example, based on an analogue signal from a patient. Analogue portion extraction unit 705 obtains a waveform portion or point by using a timing window, such as a 50 mS window for a QRS complex. Voltage adjustment module 713 adjusts a trigger signal to be in the same range as an original signal, e.g. using a maximum voltage adjustment of 50-75% of previous ECG heart beat maximum amplitude voltage (typically an ECG voltage range is fixed). Phase detector 709 determines a timing difference and latency between two signals, via which time adjustment and jitter of a hardware circuit is determined. The time adjustment compensates for jitter, due to a time clock, component characteristics, sampling rate changes, signal noise, circuit PCB and layout variation.

Figure 8:
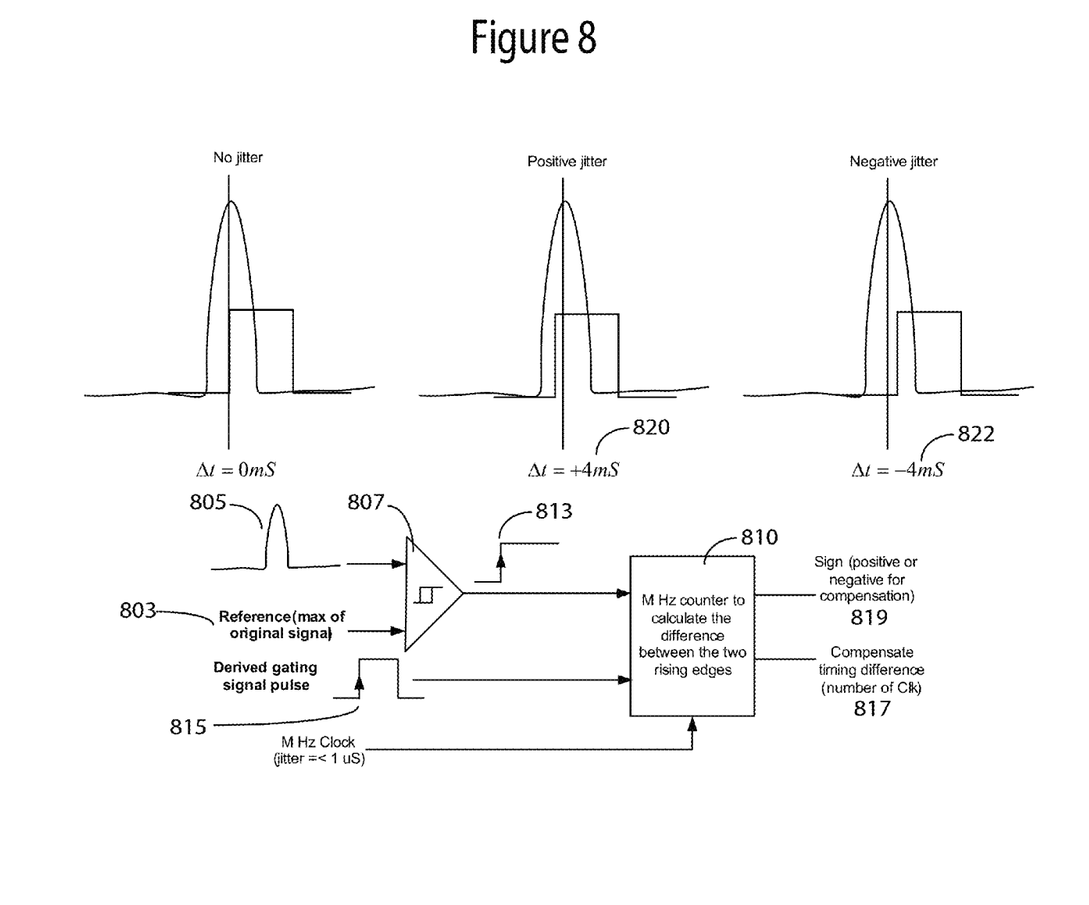
FIG. 8 shows system jitter detection and compensation, according to invention principles.

FIG. 8 shows system trigger signal jitter detection and compensation providing data comprising an output timing difference used to adjust an image acquisition trigger pulse phase (latency) to achieve image acquisition trigger timing compensation. A reference signal 803 (99% of the maximum amplitude of an original signal) is compared with R wave 805 by Schmitt trigger comparator 807 to derive rising edge 813 which indicates R wave position. Rising edge 813 and rising edge 815 of a derived gating signal pulse are both used to trigger (on and off, respectively) a clock counter device 810 to generate a timing difference 817 (e.g. +4 ms 820, −4 ms 822) and associated sign 819. Derived time difference 817 represents circuit delay and sign 819 (positive and negative) indicates whether timing difference 817 positive or negative (e.g., if derived gating comes early, then the time difference is positive).

Figure 9:
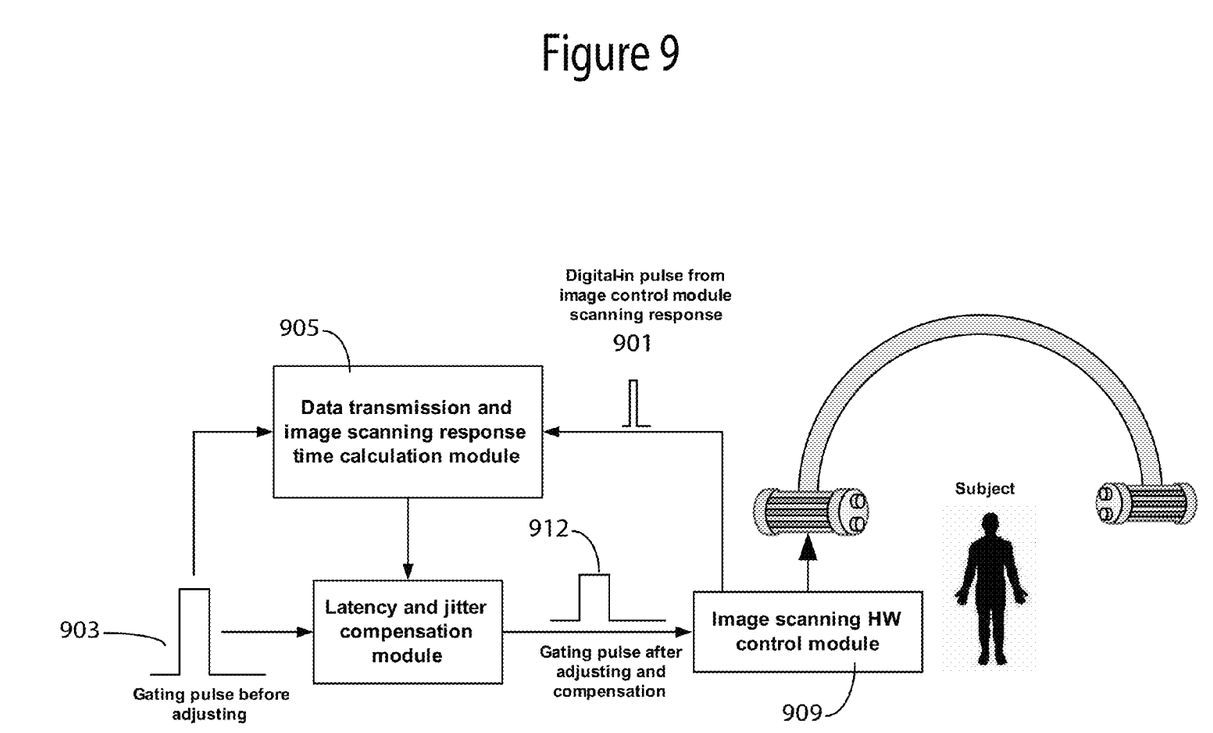
FIG. 9 shows a system for dynamic adaptive data transmission pipeline jitter and measurement and compensation, according to invention principles.

FIG. 9 shows a closed loop system for dynamic adaptive data transmission pipeline jitter and measurement used to determine a time duration for compensation. System 10 (FIG. 1) provides trigger pulse compensation to compensate for time delay comprising an interval between output of a trigger pulse (and image acquisition) subject to data transmission delay, image scanning circuit response time, waveform portion or point detection delay and hardware jitter compensation. System 10 uses a closed feedback loop to adaptively and continuously calculate a time duration representing time delay and associated jitter. If the gating signal and image system employ peer to peer (point to point) communication with no other data traffic in data transmission, total time duration of pipeline jitter and scanning response time is typically fixed. System 10 in a complicated case may use a dynamic adaptive calculation to derive accurate timing and gating for image scanning.

Data transmission and image scanning response time calculation unit 905 compares delay between the two pulses (original gating pulse 903 and digital pulse 901 from image system 909 used for triggering image acquisition) and generates a compensation time duration in response to the comparison. Latency and jitter compensation unit 907 adjusts trigger pulse 903 using the compensation time duration compensating for data pipeline and image system response delay determined by unit 905 and provides adjusted image acquisition trigger pulse 912 to imaging system control unit 909.

Figure 10:
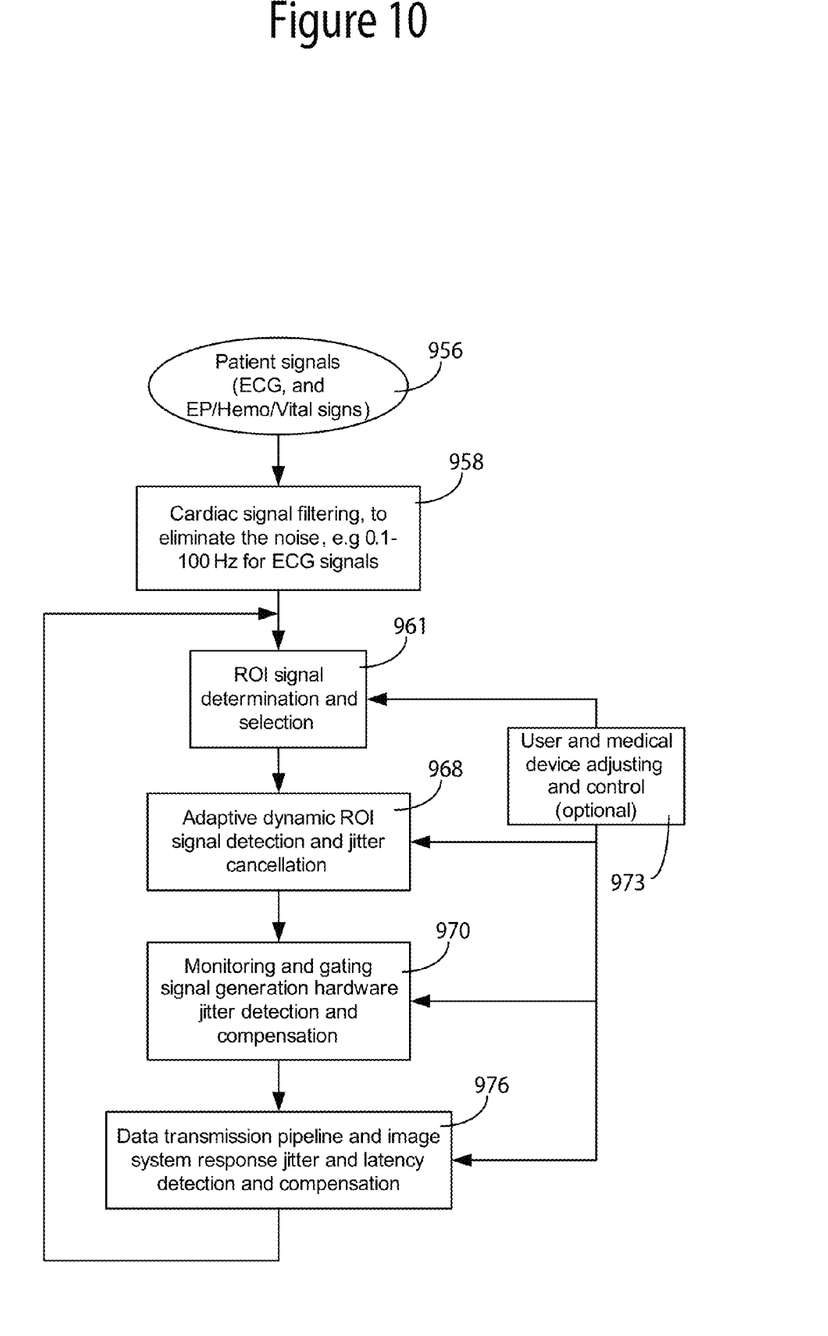
FIG. 10 shows a flowchart of a process for compensation for variation in waveform segment or point detection, hardware delay and data transmission delay, according to invention principles.

FIG. 10 shows a flowchart of a process performed by system 10 (FIG. 1) for compensation for variation in waveform segment or point detection, hardware delay and data transmission delay. Interface 15 in step 956 buffers and digitizes a non-invasive blood pressure amplitude signal, blood oxygen saturation (SPO2) signal, surface ECG signal, ICEG signals, respiration waveform signals and other vital sign signals. System 10 provides compensation for different kinds of jitter that occurs in processing hardware and scanning devices. Interface 15 in step 958 filters the received signal data using a filter adaptively selected in response to data indicating clinical application to remove patient movement and respiratory artifacts as well as power line noise. For example, a filter bandwidth 0.1-100 Hz is used for ECG signals in one embodiment and different filtering bandwidths are used for different types of signals. System 10 adjusts jitter detection and time latency, duration compensation by adding additional delay offsets. In step 961 signal processor 15 performs signal segmentation, such as of, P, Q, R, S, T, U waves in an electrophysiological signal using a known peak detector and by identifying peaks of signals by segmenting a signal represented by sampled data into windows where the waves are expected and by identifying the peaks within the windows, as previously described. The system detects P wave, Q wave, R wave, T wave, S wave and U wave segments of a received signal data by detecting peaks as previously described.

In step 961, device 30 selects a particular point of a particular signal to process for jitter compensation. In step 968, device 30 detects and compensates for jitter in segmentation, specifically in detection of a particular signal segment and point. In step 970 device 30 detects processing hardware jitter and generates a compensation timing signal compensating for segmentation and processing hardware jitter. In step 976 device 30 and unit 39 uses a feedback image acquisition trigger signal for adjusting the generated compensation timing signal for transmission pipeline and image system response jitter and latency. The process is repeated from step 961 for continuous signal jitter compensation of multiple different signals. In step 973 device 30 updates settings of the jitter compensation system used in signal segmentation and jitter detection and timing signal generation and adjusts steps 961, 968, 970 and 976.

Figure 11:
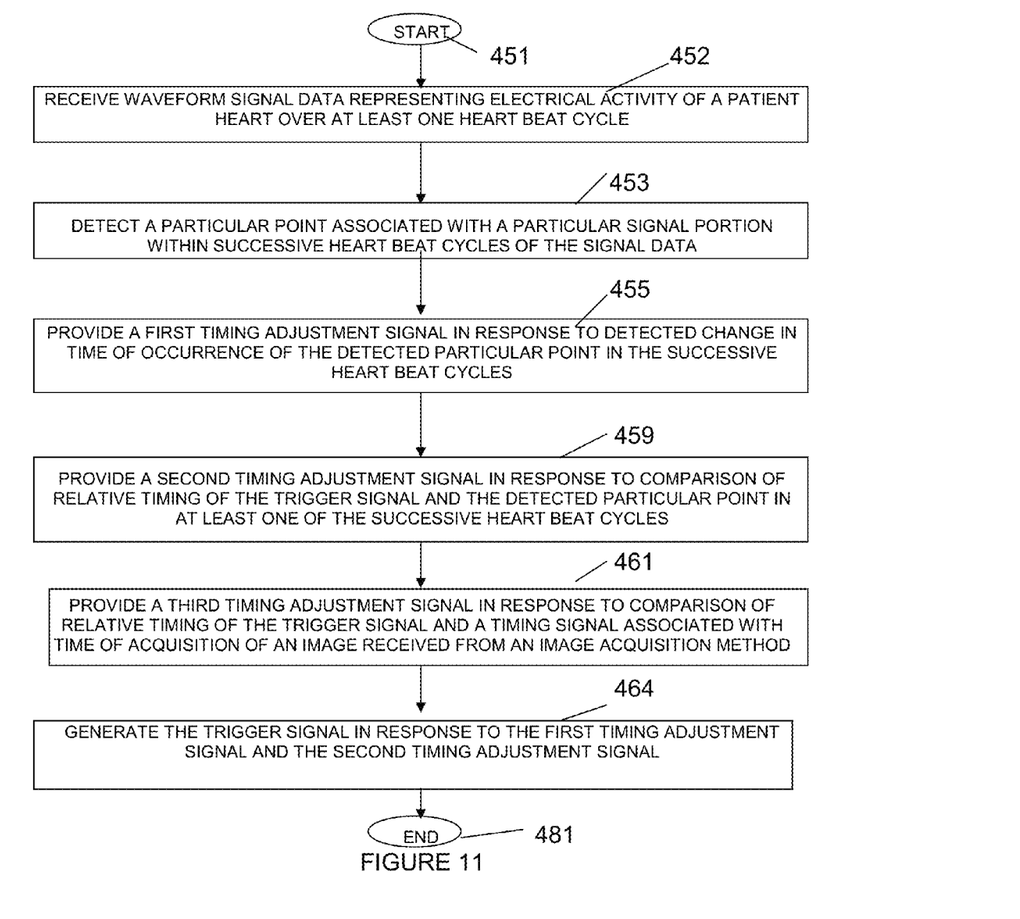
FIG. 11 shows a flowchart of a process used by a system for providing an image acquisition trigger signal compensated for signal processing time delay, according to invention principles.

FIG. 11 shows a flowchart of a process used by a system for providing an image acquisition trigger signal compensated for signal processing time delay. In step 452 following the start at step 451, interface 15 receives waveform signal data representing electrical activity of a patient heart over at least one heart beat cycle. Detector 27 in step 453 detects a particular point associated with a particular signal portion within successive heart beat cycles of the signal data. A first time variation detector in detectors 20 in step 455 provides a first timing adjustment signal in response to detected change in time of occurrence of the detected particular point in the successive heart beat cycles. In one embodiment, the first time variation detector provides the first timing adjustment signal of a current heart cycle by determining an adjustment of the detected time of occurrence of the detected particular point using a weighted combination of time intervals. The time intervals comprise time intervals between a predetermined amplitude level of the waveform signal and the particular point and occurring either side of the particular point in a heart cycle prior to the current heart cycle. The time adjustment associated with the first timing adjustment signal compensates for jitter occurring in detecting a portion of the waveform signal data representing electrical activity of the patient heart.

A second time variation detector in detectors 20 in step 459 provides a second timing adjustment in response to comparison of relative timing of the trigger signal and the detected particular point in at least one of the successive heart beat cycles. The time adjustment associated with the second timing adjustment signal compensates for jitter occurring in circuitry hardware. A third time variation detector in detectors 20 in step 461 provides a third timing adjustment signal in response to comparison of relative timing of the trigger signal and a timing signal associated with time of acquisition of an image received from an image acquisition system. The time adjustment associated with the third timing adjustment signal compensates for delay between relative timing of the trigger signal and a timing signal associated with time of acquisition of an image.

Output processor 39 in step 464 generates the trigger signal in response to the first timing adjustment signal, the second timing adjustment signal and the third timing adjustment signal. In one embodiment, output processor 39 generates the trigger signal by summing time adjustments associated with the first timing adjustment signal, the second timing adjustment signal and the third timing adjustment signal to provide a predicted time of acquisition of an image within a heart cycle. The process of FIG. 11 terminates at step 481.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. A histogram of an image is a graph that plots the number of pixels (on the y-axis herein) in the image having a specific intensity value (on the x-axis herein) against the range of available intensity values. The resultant curve is useful in evaluating image content and can be used to process the image for improved display (e.g. enhancing contrast).

The system and processes of FIGS. 1-11 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system compensates for image acquisition ECG trigger pulse (especially for P wave, R wave, T wave) timing jitter by automatically adaptively, dynamically compensating for signal generation and transmission jitter and latency and improves accuracy of time stamps associated with acquired images. Further, the processes and applications may, in alternative embodiments, be located on one or more (e.g., distributed) processing devices on a network linking the units FIG. 1. Any of the functions and steps provided in FIGS. 1-11 may be implemented in hardware, software or a combination of both. No claim element herein is to be construed under the provisions of 35 U.S.C. 112, sixth paragraph, unless the element is expressly recited using the phrase "means for."

What is claimed is:

1. A system for providing an image acquisition trigger signal compensated for signal processing time delay, comprising:
   a processor programmed to;
   receive waveform signal data representing electrical activity of a patient heart over at least one heart beat cycle;
   detect a particular point associated with a particular signal portion within successive heart beat cycles of said signal data;
   provide a first timing adjustment signal in response to detected change in time of occurrence of the detected particular point in said successive heart beat cycles;
   provide a second timing adjustment signal in response to comparison of relative timing of said image acquisition trigger signal and said detected particular point in at least one of said successive heart beat cycles;
   provide a third timing adjustment signal in response to comparison of relative timing of said image acquisition trigger signal and a timing signal associated with time of acquisition of an image received from an image acquisition system;
   an output processor configured to generate said image acquisition trigger signal in response to said first timing adjustment signal and said second timing adjustment signal; and
   wherein said output processor generates said image acquisition trigger signal by summing time adjustments associated with said first timing adjustment signal, said second timing adjustment signal and said third timing adjustment signal to provide a predicted time of acquisition of an image within a heart cycle.

2. A system according to claim 1, wherein the processor further programmed to provide said first timing adjustment signal of a current heart cycle by determining an adjustment of said detected time of occurrence of the detected particular point using a weighted combination of time intervals, said time intervals, comprising time intervals between a predetermined amplitude level of said waveform signal and said particular point and occurring either side of said particular point in a heart cycle prior to said current heart cycle.

3. A system according to claim 1, wherein
   said first timing adjustment signal compensates for jitter occurring in detecting a portion of said waveform signal data representing electrical activity of said patient heart and
   said second timing adjustment signal compensates for jitter occurring in circuitry hardware.

4. A system according to claim 3, wherein said output processor generates said image acquisition trigger signal by summing a time adjustments associated with said first timing adjustment signal and said second timing adjustment signal.

5. A system according to claim 3,
   wherein said third timing adjustment signal compensates for delay between relative timing of said image acquisition trigger signal and a timing signal associated with time of acquisition of an image.

6. A method for providing an image acquisition trigger signal compensated for signal processing time delay, comprising:
   providing a processor that is programmed to;
   receive waveform signal data representing electrical activity of a patient heart over at least one heart beat cycle;
   detect a particular point associated with a particular signal portion within successive heart beat cycles of said signal data;
   provide a first timing adjustment signal in response to detected change in time of occurrence of the detected particular point in said successive heart beat cycles;
   provide a second timing adjustment signal in response to comparison of relative timing of said image acquisition trigger signal and said detected particular point in at least one of said successive heart beat cycles;
   provide a third timing adjustment signal in response to comparison of relative timing of said image acquisition trigger signal and a timing signal associated with time of acquisition of an image received from an image acquisition method;
   generating, through an output processor, said image acquisition trigger signal in response to said first timing adjustment signal and said second timing adjustment signal; and
   wherein said output processor generates said image acquisition trigger signal by summing time adjustments associated with said first timing adjustment signal, said second timing adjustment signal and said third timing adjustment signal to provide a predicted time of acquisition of an image within a heart cycle.

7. A method according to claim 6, the processor further programmed to provide said first timing adjustment signal of a current heart cycle by determining an adjustment of said detected time of occurrence of the detected particular point using a weighted combination of time intervals, said time intervals, comprising time intervals between a predetermined amplitude level of said waveform signal and said particular point and occurring either side of said particular point in a heart cycle prior to said current heart cycle.

8. A method according to claim 6, wherein
   said first timing adjustment signal compensates for jitter occurring in detecting a portion of said waveform signal data representing electrical activity of said patient heart; and
   said second timing adjustment signal compensates for jitter occurring in circuitry hardware.

9. A method according to claim 8, including the activity of generating, through the output processor, said image acquisition trigger signal by summing a time adjustments associated with said first timing adjustment signal and said second timing adjustment signal.

10. A method according to claim 8,
wherein said third timing adjustment signal compensates for delay between relative timing of said image acquisition trigger signal and a timing signal associated with time of acquisition of an image.

* * * * *